United States Patent [19]

Shibata et al.

[11] Patent Number: 4,804,759
[45] Date of Patent: Feb. 14, 1989

[54] PYRIMIDINE COMPOUND

[75] Inventors: Toshihiro Shibata; Norio Kurosawa, both of Urawa, Japan

[73] Assignee: Adeka Argus Chemical Co., Ltd., Tokyo, Japan

[21] Appl. No.: 185,097

[22] Filed: Apr. 22, 1988

[30] Foreign Application Priority Data

May 27, 1987 [JP] Japan ............................ 62-130294
Sep. 29, 1987 [JP] Japan ............................ 62-244781

[51] Int. Cl.$^4$ .................. G02F 1/13; C09K 19/34; C07D 239/02
[52] U.S. Cl. ................ 544/335; 252/299.01; 252/299.5; 252/299.61; 350/350 R; 350/350 S
[58] Field of Search ............... 252/299.61, 299.01, 252/299.5; 350/350 R, 350 S; 544/335, 242

[56] References Cited

U.S. PATENT DOCUMENTS

| 4,723,005 | 2/1988 | Huymh-ba et al. | 252/299.61 |
| 4,725,688 | 2/1988 | Thguchi et al. | 252/299.61 |
| 4,728,458 | 2/1988 | Higuchi et al. | 252/299.01 |
| 4,732,699 | 3/1988 | Higuchi et al. | 252/299.01 |

FOREIGN PATENT DOCUMENTS

| 225195 | 6/1987 | European Pat. Off. | 252/299.61 |
| 3515373 | 11/1986 | Fed. Rep. of Germany | 252/299.61 |
| 61271279 | 12/1986 | Japan | 252/299.61 |
| 8606401 | 11/1986 | PCT Int'l Appl. | 252/299.61 |

Primary Examiner—Teddy S. Gron
Attorney, Agent, or Firm—Frishauf, Holtz, Goodman & Woodward

[57] ABSTRACT

The present invention discloses an optically active pyrimidine compound represented by the following general formula:

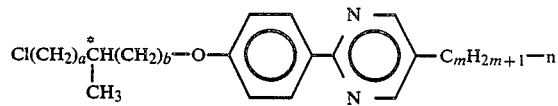

wherein, a is 2 or 3, b is 2 or 3 and $a+b=5$; m is 4 to 18; and $\overset{*}{C}$ represents an asymmetric carbon atom.

The pyrimidine compound of the present invention is a liquid crystal compound useful as an electrooptic element wherein the response of the ferroelectric liquid crystal to an electric field is utilized.

12 Claims, No Drawings

PYRIMIDINE COMPOUND

BACKGROUND OF THE INVENTION

1. Field of the Invention

This invention releates to an optically active pyrimidine compound which is a liquid crystal compound useful as an electrooptic element wherein the response of the ferroelectric smectic liquid crystal to an electric field is utilized.

2. Description of the Prior Art

Liquid crystals have been employed as various electrooptic elements such as a display device of a watch or an electronic calculator. Most of liquid crystal display devices which have been put into practical use hitherto are those wherein the dielectric orientation effect of a nematicor cholesteric liquid crystal is utilized. However, the application of these liquid crystals to a display device involving a large number of pixels is accompanied by some troubles such as a low response, poor contrast caused by the lack of drive margin and unsatisfactory visual angles. Therefore, there has been frequently attempted to develop a MOS or TFT panel involving formation of a switching device for each pixel.

U.S. Pat. No. 4,367,924 has disclosed a liquid crystal device wherein a smectic phase based on a novel displaying principle is used to thereby overcome the disadvantages as described above.

Further it has been known that a liquid crystal compound exhibiting a C* or H phase consisting of optically active molecules generally has an electrical dipole density P and is ferroelectric. Such a chiral smectic liquid crystal having electrical dipoles is more strongly affected by an electric field than dielectric anisotropic ones. As a result, the polarity of P is made parallel to the direction of the electric field. Thus the direction of the molecules can be controlled by reversing the direction of the applied electric field. Then the average change in the direction of the major axes of these molecules is detected with the use of two polarizing plates. Thus the liquid crystal can be used as an electrooptic element.

The effect of the spontaneous polarization of this electrooptic element, wherein the response of the smectic C* or H phase to an electric field is utilized, and the electric field exert an action $10^3$ to $10^4$ times as high as those of dielectric anisotropic ones. Thus the former shows a high-speed response compared with a TN liquid crystal device. Further it is possible to impart thereto a memory function by appropriately controlling the orientation. Therefore it is expected to apply the same to a high-speed optical shutter or to a display of a large capacity.

There have been synthesized various chiral smectic liquid crystal compounds having a ferroelectricity and the properties therefof have been studied.

For example, an optically active 2-(4-alkoxyphenyl)-5-alkylpyrimidine compound has been proposed as a compound which is stable to water and shows a chiral smectic phase within a wide range of temperature in Japanese Patent Laid-Open No. 93170/1986.

However, each compound as described above is available only within a restricted range of temperature. Namely, its insufficient properties, in particular, at a low temperature make it unsatisfactory from the practical viewpoint.

SUMMARY OF THE INVENTION

It is the main object of the present invention to provide a compound useful as a liquid crystal which is suitable for preparing a composition available over an unlimited temperature range and, in particular, having a liquid crystal temperature lower than room temperature.

We have attempted to develop a pyrimidine liquid crystal compound which shows a chiral smectic phase over a wide temperature range. As a result, we have found that an optically active pyrimidine compound of the following general formula, wherein an alkyl group has an asymmetric carbon atom and a chlorine atom bonded to the terminal carbon atom, shows a chiral smectic phase over a wide range of temperature involving, in particular, a low temperature region, thus completing the present invention.

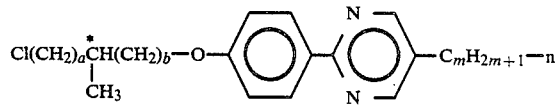

wherein, a is 2 or 3, b is 2 or 3 and a+b=5; m is 4 to 18; and C represents an asymmetric carbon atom.

DETAILED DESCRIPTION OF THE INVENTION

The compound of the present invention as represented by the above general formula can be prepared by a common method used in synthesizing phenylpyrimidine compounds.

For example, it may be prepared by etherifying 5-alkyl-2-(4-hydroxyphenyl)pyrimidine with 6-chloro-3-methylhexanol or 6-chloro-4-methylhexanol; or by etherifying 4-cyanophenol with 6-chloro-3-methylhexanol or 6-chloro-4-methylhexanol and converting the resulting product into pyrimidine in a conventional manner.

A 5-alkyl-2-(4-hydroxyphenyl)pyrimidine compound may be prepared by a conventional method comprising, for example, converting 4-cyanophenol into a benzyl ether in a conventional manner, converting the resulting ether into 4-benzyloxy-benzamidine hydrochloride, reacting the obtained product with an n-alkylmalonic acid diester to give a 2-(4-benzyloxyphenyl)-4,6-dihydroxy-5-n-alkyl-pyrimidine and then chlorinating and reducing the product.

The obtained compound of the present invention as represented by the above general formula can be used alone as a liquid crystal material. Alternately it can be mixed with other liquid crystal compound(s).

To further illustrate the present invention, the following Examples will be given.

EXAMPLE 1

Synthesis of (R)-2-(4'-(6"-chloro-4"-methylhexyloxy)-phenyl)-5-n-octyl-pyrimidine

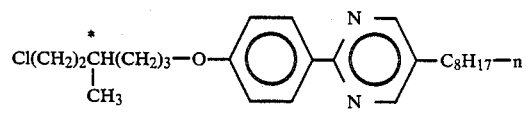

0.25 g of 55% sodium hydride and 7 ml of dimethylformamide were weighed out and a solution of 1.3 g of 2-(4'-hydroxyphenyl)-5-n-octyl-pyrimidine in 2 ml of dimethylformamide was added dropwise thereto under ice cooling. After the completion of the addition, the resulting mixture was stirred at room temperature for one hour.

Then a solution of 1.4 g of p-toluenesulfonate of (R)-(−)-6-chloro-4-methylhexanol in 2 ml of dimethylformamide was added dropwise thereto and the resulting mixture was stirred at 80° C. for two hours. After cooling, the reaction mixture was poured into ice/water, extracted with diethylether and dried followed by removal of solvent.

The product was purified on a silica gel column with the use of hexane/ether (4/1) as a developing solvent. Thus 1.2 g of (R)-2-(4'-(6''-chloro-4''-methylhexyloxy)-phenyl)-5-n-octyl-pyrimidine was obtained.

Infrared spectroscopy (cm$^{-1}$): 2920(s), 2850(m), 1610(m), 1580(s), 1430(vs), 1250(s), 1170(m) and 800(m).

Optical rotation: $[\alpha]_D = +3.26°$ (C=1, CHCl$_3$ solution, 24° C.).

This compound was poured into a transparent glass cell and the following phase transition was observed under a polarization microscope.

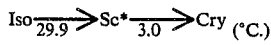

Iso: isotropic, Sc*: chiral smectic Cry: crystal

It has been confirmed that the above compound of the present invention shows an Sc* phase over a wide temperature range, i.e., over 25° C. involving a temperature as low as 4° C., which obviously suggests that it is suitable for the preparation of a composition showing a low liquid crystal temperature.

In contrast thereto, the compounds as described in Japanese Patent Laid-Open Nos. 93170/1986 and 129169/1986, wherein an alkyl groups have no chlorine atom, shows an Sc* phase at a temperature exceeding approximately 15° C. Thus the physical properties thereof at a low temperature are unsatisfactory.

EXAMPLE 2

Synthesis of (R)-2-(4'-(6''-chloro-4''-methylhexyloxy)-phenyl)-5-n-decyl-pyrimidine

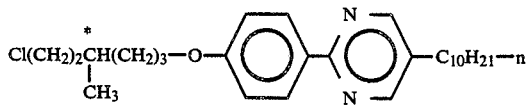

The procedure of Example 1 was followed except that the 2-(4'-hydroxyphenyl)-5-n-octyl-pyrimidine was replaced by 2-(4'-hydroxyphenyl)-5-n-decyl-pyrimidine to therby give the title compound.

Infrared spectroscopy (cm$^{-1}$): 2900(vs), 2850(s), 1600(w), 1580(m), 1430(s), 1250(m), 1170(m) and 800(s).

Optical rotation: $[\alpha]_D = +3.23°$ (C=1, CHCl$_3$ solution, 25° C.).

Phase transition

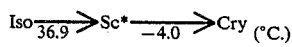

It has been confirmed that the above compound of the present invention shows an Sc* phase over a wide temperature range, i.e., over 40° C. involving a temperature as low as −4° C., which obviously suggests that it is suitable for the preparation of a composition showing a low liquid crystal temperature.

EXAMPLE 3

Synthesis of (R)-2-(4'-(6''-chloro-3''-methylhexyloxy)-phenyl)-5-n-octyl-pyrimidine

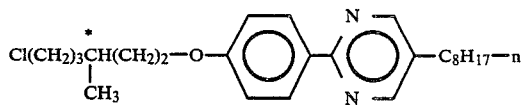

0.20 g of 55% sodium hydride and 5 ml of dimethylformamide were weighed out and a solution of 1.04 g of 2-(4'-hydroxyphenyl)-5-n-octyl-pyrimidine in 2 ml of dimethylformamide was added dropwise thereto under ice cooling. After the completion of the addition, the resulting mixture was stirred at room temperature for one hour.

Then a solution of 1.12 g of p-toluenesulfonate of (R)-6-chloro-3-methylhexanol in 2 ml of dimethylformamide amide was added dropwise thereto and the resulting mixture was stirred at 80° C. for two hours. After cooling, the reaction mixture was poured into ice/water, extracted with diethylether and dried followed by removal of solvent.

The product was purified on a silica gel column with the use of hexane/ether (85/15) as a developing solvent. Thus 0.92 g of (R)-2-(4'-(6''-chloro-3''-methylhexyloxy)phenyl)-5-n-octyl-pyrimidine was obtained.

Infrared spectroscopy (cm$^{-1}$): 2930(s), 2860(s), 1610(s), 1585(s), 1430(vs), 1250(vs), 1170(s), 800(m), 720(w) and 650(w).

Optical rotation: $[\alpha]_D = +5.45°$ (C=1, CHCl$_3$ solution, 26° C.).

Phase transition

N*: chiral nematic

It has been confirmed that the above compound of the present invention shows an Sc* phase over a wide temperature range, i.e., over 25° C. involving a temperature as low as below −5° C., which obviously suggests that it is suitable for the preparation of a composition showing a low liquid crystal temperature.

EXAMPLE 4

Synthesis of (R)-2-(4'-(6''-chloro-3''-methylhexyloxy)-phenyl)-5-n-decyl-pyrimidine

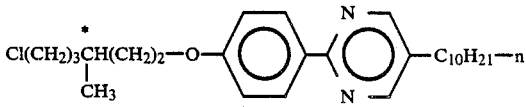

The procedure of Example 3 was followed except that the 2-(4'-hydroxyphenyl)-5-n-octyl-pyrimidine was replaced by 2-(4'-hydroxyphenyl)-5-n-decyl-pyrimidine to therby give the title compound.

Infrared spectroscopy (cm$^{-1}$): 2910(s), 2850(s), 1600(s), 1580(s), 1425(vs), 1250(vs), 1170(s), 800(m), 720(w) and 650(w).

Optical rotation: [α]$_D$=+5.02° (C=1, CHCl$_3$ solution, 25° C.).
Phase transition

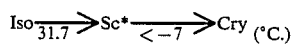

It has been confirmed that the above compound of the present invention shows an Sc* phase over a wide temperature range, i.e., over 25° C. involving a temperature as low as below −5° C., which obviously suggests that it is suitable for the preparation of a composition showing a low liquid crystal temperature.

Thus the compound of the present invention is useful as a liquid crystal compound suitable for the preparation of a composition having a liquid crystal temperature lower than room temperature and as a blending agent suitable for the preparation of a composition having a liquid crystal temperature lower than room temperature.

What is claimed is:

1. An optically active pyrimidine compound represented by the following general formula:

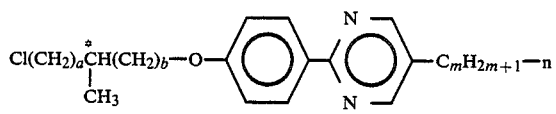

wherein, a is 2 or 3, b is 2 or 3 and a+b=5; m is 4 to 18; and C represents an asymmetric carbon atom.

2. A pyrimidine compound as set forth in claim 1 in which a is 2 and b is 3.

3. A pyrimidine compound as set forth in claim 1 in which a is 3 and b is 2.

4. A pyrimidine compound as set forth in any one of claims 1, 2 or 3 in which m is 6 to 12.

5. A pyrimidine compound as set forth in any one of claims 1, 2 or 3 in which m is 8.

6. A pyrimidine compound as set forth in any one of claims 1, 2 or 3 in which m is 10.

7. A pyrimidine compound of claim 1 represented by the following formula:

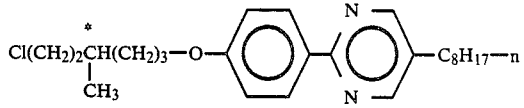

8. A pyrimidine compound of claim 1 represented by the following formula:

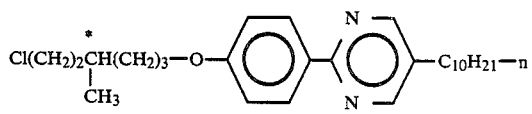

9. A pyrimidine compound of claim 1 represented by the following formula:

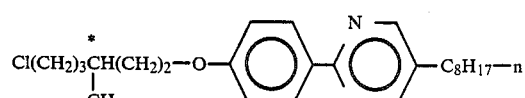

10. A pyrimidine compound of claim 1 represented by the following formula:

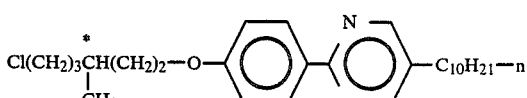

11. A pyrimidine compound as set forth in claim 4 in which m is 8.

12. A pyrimidine compound as set forth in claim 4 in which m is 10.

* * * * *